United States Patent [19]
Lindner et al.

[11] 4,448,643
[45] May 15, 1984

[54] ISOLATION OF ISOBUTENE FROM C4-HYDROCARBON MIXTURES CONTAINING ISOBUTENE

[75] Inventors: Alfred Lindner, Bobenheim-Roxheim; Klaus Volkamer, Frankenthal; Ulrich Wagner, Limburgerhof, all of Fed. Rep. of Germany

[73] Assignee: BASF Aktiengesellschaft, Fed. Rep. of Germany

[21] Appl. No.: 282,746

[22] Filed: Jul. 13, 1981

Related U.S. Application Data

[63] Continuation of Ser. No. 122,067, Feb. 15, 1980, abandoned.

[30] Foreign Application Priority Data

Mar. 5, 1979 [DE] Fed. Rep. of Germany ....... 2908426

[51] Int. Cl.³ .......................... C07C 7/148; B01D 3/32
[52] U.S. Cl. ........................................ 203/34; 203/71; 203/DIG. 6; 203/DIG. 19; 203/38; 568/697; 585/864

[58] Field of Search ....................... 203/29, 38, 71, 99, 203/34, DIG. 6, DIG. 19; 585/864; 568/697, 699

[56] References Cited

U.S. PATENT DOCUMENTS

| | | | |
|---|---|---|---|
| 3,121,124 | 2/1964 | Verdol | 585/864 |
| 3,170,000 | 2/1965 | Verdol | 585/864 |
| 3,629,478 | 12/1971 | Haunschild | 568/697 |
| 3,634,534 | 1/1972 | Haunschild | 203/DIG. 6 |
| 3,634,535 | 1/1972 | Haunschild | 585/864 |

*Primary Examiner*—Wilbur L. Bascomb, Jr.
*Attorney, Agent, or Firm*—Keil & Witherspoon

[57] ABSTRACT

A process for isolating isobutene from C4-hydrocarbon mixtures containing isobutene by reacting the mixture with a primary alcohol in the presence of an acid condensing agent, to form the tertiary ether, separating off the unconverted hydrocarbons and decomposing the tertiary ether in the presence of an acid catalyst at an elevated temperature, wherein a primary C3- or C4-alcohol is used and the temperature at which the reaction mixture leaves the etherification stage, in which the tertiary ether is formed, is lower than the mean temperature in the etherification stage.

10 Claims, 1 Drawing Figure

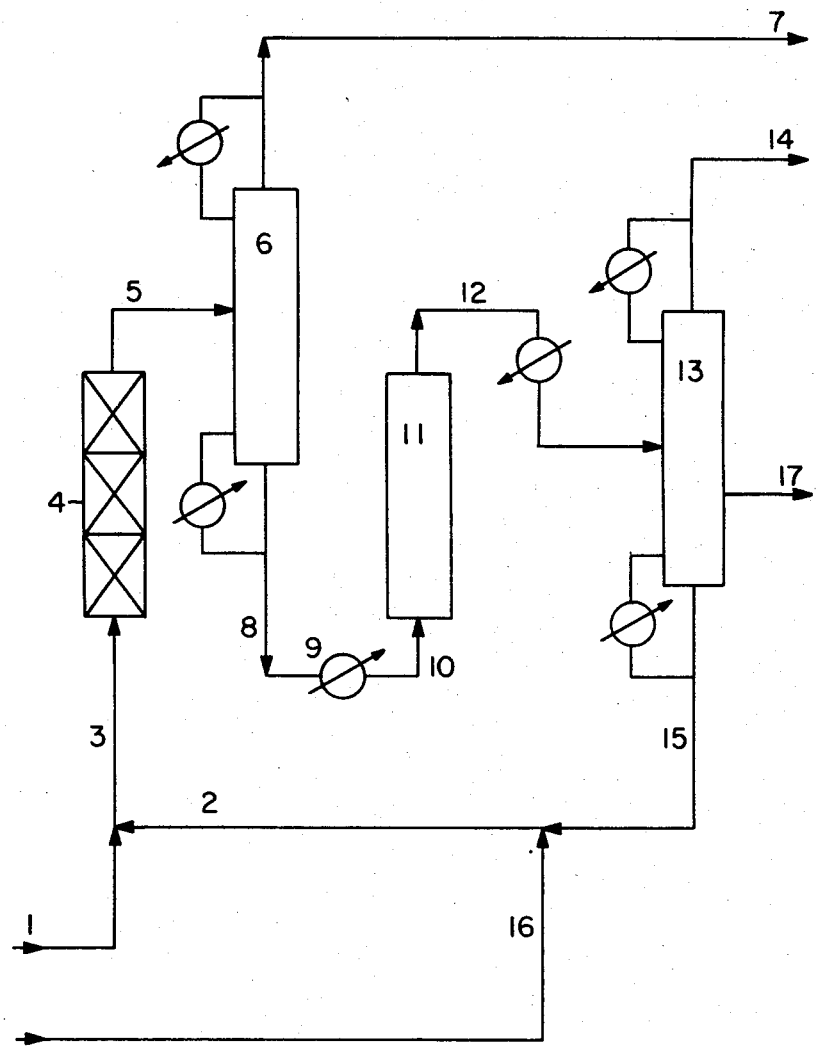

ISOLATION OF ISOBUTENE FROM C₄-HYDROCARBON MIXTURES CONTAINING ISOBUTENE

This is a continuation of application Ser. No. 122,067, filed Feb. 15, 1980, now abandoned.

The present invention relates to a process for isolating isobutene from $C_4$-hydrocarbon mixtures containing isobutene by reacting the mixture with a primary $C_3$- or $C_4$-alcohol and decomposing the resulting tertiary ether at an elevated temperature.

The isolation of isobutene from $C_4$-hydrocarbon mixtures by sulfuric acid extraction processes has been disclosed. In these processes, very concentrated sulfuric acid must be used and hence the equipment has to be constructed of expensive materials. Since, furthermore, side-reactions of isobutene, for example dimerization, polymerization, hydration and the like, occur during the extraction, the sulfuric acid extraction process is not always satisfactory in respect of yield and quality of the products.

Further, a process for isolating isobutene has been disclosed, for example in U.S. Pat. No. 3,170,000, in which, in a first stage, isobutene is reacted with methanol, and, in a second stage, the methyl tert.-butyl ether formed is decomposed into methanol and isobutene. However, the conventional processes have the disadvantage that if $C_4$-hydrocarbon mixtures containing isobutene are used as the starting material, methanol forms azeotropic mixtures with the $C_4$-hydrocarbons, so that separating the methanol from the reaction mixture obtained after the etherification stage becomes very difficult and it is necessary, for example, to interpolate an expensive water wash. A further disadvantage of the conventional processes is that the yield of the reaction of isobutene with the alcohol, to form the tertiary ether, is unsatisfactory and hence, if a $C_4$-hydrocarbon mixture containing isobutene is used as the starting material, a $C_4$-hydrocarbon mixture of unconverted hydrocarbon which still has an unsatisfactorily high isobutene content is obtained from the reaction mixture resulting after the etherification.

It is an object of the present invention to provide a process for isolating isobutene from $C_4$-hydrocarbon mixtures containing isobutene, wherein the stage of etherifying the isobutene with the primary alcohol gives a good yield of the tertiary ether and wherein a raffinate which is virtually free from primary alcohol can be obtained, by simple distillation, from the reaction mixture obtained after the etherification stage, without interpolating a water wash.

We have found that this and other objects are achieved, according to the invention, by a process for isolating isobutene from $C_4$-hydrocarbon mixtures containing isobutene by reacting the mixture with a primary alcohol in the presence of an acid condensing agent, to form the tertiary ether, separating off the unconverted hydrocarbons and decomposing the tertiary ether in the presence of an acid catalyst at an elevated temperature, wherein a primary $C_3$- or $C_4$-alcohol is used and the temperature at which the reaction mixture leaves the etherification stage, in which the tertiary ether is formed, is lower than the mean temperature in the etherification stage.

Using the novel process, a virtually alcohol-free $C_4$-hydrocarbon raffinate can be isolated from the reaction mixture, obtained after the etherification stage, by simple distillation without interpolating a water wash, since unconverted primary $C_3$- or $C_4$-alcohol surprisingly does not form an azeotrope with the $C_4$-hydrocarbons. In general, the concentration of $C_3$- or $C_4$-alcohol in the $C_4$-hydrocarbon raffinate is at most 50 ppm by weight, preferably at most 20 ppm by weight, in particular at most 5 ppm by weight. Hence, the expense entailed in the separation is substantially less in the process according to the invention than in the conventional process. A further advantage of the process according to the invention is that, even when using a small reactor, the conversion of the isobutene, present in the initial $C_4$-hydrocarbon mixture, to the tertiary ether by reaction with the primary alcohol is substantially increased, in a simple manner, so that a $C_4$-hydrocarbon raffinate consisting of the unconverted hydrocarbons, with a substantially reduced isobutene content, can be isolated from the reaction mixture obtained after the etherification. The loss of isobutene during the reaction to give the tertiary ether can thereby be substantially reduced. The $C_4$-hydrocarbon raffinate obtained, which is substantially free from isobutene, is exceptionally suitable for certain applications for which a $C_4$-hydrocarbon raffinate of very low isobutene content is required, for example as a starting material for the preparation of sec.-butanol, methyl ethyl ketone, but-1-ene, octenes or maleic anhydride.

It is a further advantage of the novel process that butadiene-containing $C_4$-fractions, as obtained, for example, from ethylene plants or butane/butene dehydrogenation plants can be used directly as the $C_4$-hydrocarbon mixture. It is not necessary first to extract the butadiene from the $C_4$-fraction.

Using the process according to the invention, isobutene is obtained in high yield. It is surprising that this high yield is achievable using a higher alcohol, such as a primary $C_3$- or $C_4$-alcohol, since U.S. Pat. No. 3,170,000 discloses, in particular in Table I, that on reacting $C_5$-hydrocarbon mixtures with alcohols, substantially poorer yields of tertiary ether are obtained when using $C_3$- or $C_4$-alcohols than when using ethanol or methanol. By contrast, using the process according to the invention, the conversion, in the etherification reaction, of the isobutene contained in the $C_4$-hydrocarbon mixture to the $C_3$- or $C_4$-alkyl tert.-butyl ether is in general not less than 90% and preferably not less than 95%.

$C_4$-Hydrocarbon mixtures containing isobutene which are suitable for the process according to the invention are obtained, for example, from the thermal or catalytic cracking of petroleum products, from the preparation of ethylene by pyrolysis of liquefied petroleum gas (LPG), naphtha, gas oil or the like, or from the catalytic dehydrogenation of n-butane and/or n-butene. These $C_4$-hydrocarbon mixtures as a rule contain olefinic and paraffinic $C_4$-hydrocarbons in addition to isobutene and may furthermore contain butadiene, for example in amounts of up to 70 percent by weight, and higher acetylenes, e.g. but-1-yne and butenyne. $C_4$-Hydrocarbon mixtures containing butadiene can be used either as such or after first removing the butadiene from the $C_4$-hydrocarbon mixture, for example by extracting it with a selective solvent. The $C_4$-hydrocarbon mixtures can furthermore contain $C_3$-hydrocarbons, e.g., propane, propene and/or propyne, for example in amounts of up to 10 percent by weight. The $C_4$-hydrocarbon mixtures in general contain from 5 to 95 percent by weight, preferably from 10 to 90 percent by weight, especially from 20 to 70 percent by weight, of isobutene. The use of C$_4$-hydrocarbon mixtures which in addition to isobutene contain n-butane, isobutane, but-1-ene, trans-but-2-ene and cis-but-2-ene, with or without buta-1,3,-diene, is preferred.

The primary C$_3$- or C$_4$-alcohols (ie. alcohols of 3 or 4 carbon atoms) used according to the invention are in general n-propanol, n-butanol or isobutanol, preferably n-propanol or isobutanol, and more especially isobutanol. The alcohols are used as, for example, technical-grade products of the usual purity, for example products which are not less than 95% pure and preferably not less than 98% pure.

Examples of suitable acid condensing agents for the etherification stage are mineral acids, eg. sulfuric acid and phosphoric acid, organic sulfonic acids, eg. benzenesulfonic acid and p-toluenesulfonic acid, acid aluminum salts, acid catalysts of the Friedel-Crafts type, eg. copper(II) chloride and iron(II) chloride, and, preferably, ion exchangers in the hydrogen form. Examples of suitable ion exchangers are sulfonated coal, zeolites, sulfonated phenol-formaldehyde resins, sulfonated resins derived from coumarone-indene condensation products and, in particular, sulfonated polystyrene resins, eg. nuclear-sulfonated crosslinked styrene-divinylbenzene copolymers. If a liquid or dissolved acid condensing agent is used, the amount of the said agent is in general from about 0.001 to 0.9 l, preferably 0.01 to 0.7 l, per 1 of reactor volume. If a solid acid condensing agent is used, the amount of the latter is in general form 0.01 to 1 l of bulk volume per 1 of reactor volume. The acid condensing agents may be used as such or on a carrier. Examples of suitable carriers are alumina, silica and active charcoal.

Examples of reactors which may be used for the etherification stage are stirred kettle reactors and flow tube reactors, for example a loop reactor. Preferably, fixed bed reactors are employed as the flow tube reactors.

It can be of advantage to provide several reaction zones in series in the etherification stage, in general from 2 to 10 reaction zones, preferably from 2 to 6 reaction zones. Where this is the case, it can be advantageous to take off a bleed-stream from one reaction zone, or from each of several or all reaction zones, and recycle it into the main stream, upstream of one of the preceding reaction zones.

To carry out the etherification, the hydrocarbon mixture is reacted with the primary C$_3$- or C$_4$-alcohol in the presence of the acid condensing agent, in general at from 20° to 120° C. The maximum temperature in the etherification stage is in general from 50° to 120° C., preferably from 70° to 120° C. The exit temperature from the etherification stage is in general from 20° to 70° C., preferably from 30° to 50° C.

The process according to the invention is carried out in such a way that the temperature at which the reaction mixture leaves the etherification stage in which the tertiary ether is formed is lower than the mean temperature in the etherification stage. In general, the former is from 3° to 30° C., preferably from 5° to 20° C., especially from 7° to 15° C., lower than the latter.

The mean temperature in the etherification stage is advantageously determined from the following equation:

$$T_m = \frac{1}{V_G} \int_{v=0}^{v=V_G} T\, dv \quad (1)$$

In equation (1) the symbols have the following meanings:

| | |
|---|---|
| $T_m$ | = mean temperature in the etherification stage |
| $T$ | = temperature at volume element v |
| $v$ | = volume |
| $V_G$ | = total volume of the etherification stage |

It follows that if, for example, stirred kettles and/or flow tubes are used for the etherification stage, the mean temperature in the latter can advantageously be found from the following equation:

$$T_m = \frac{1}{V_R} \sum_{j=0}^{j=R} V_j T_j + \frac{1}{V_S} \sum_{i=0}^{i=S} \int_{v=0}^{v=V_i} T_i\, dv \quad (2)$$

In equation (2), the symbols have the following meaning:

| | |
|---|---|
| $T_m$ | = mean temperature in the etherification stage |
| $T_j$ | = temperature in the stirred kettle j |
| $T_i$ | = temperature in the flow tube i at volume v |
| $V_i$ | = volume of the ith flow tube |
| $V_j$ | = volume of the jth stirred kettle |
| $R$ | = number of stirred kettles arranged in series in the etherification stage |
| $S$ | = number of flow tubes arranged in series in the etherification stage |
| $V_R$ | = Total volume of the stirred kettles |
| $V_S$ | = total volume of the flow tubes |

In this equation, R or S may also assume the value 0.

If only a single reaction zone is used for the etherification stage, and mean temperature in this stage, and the exit temperature from this stage, can be varied by, for example, direct cooling of the reaction zone by varying the amount of coolant, the coolant temperature and the coolant flow direction, for example by using counter-current cooling. If the etherification stage comprises several reaction zones, the mean temperature in the etherification stage and the exit temperature from the etherification stage can be varied, for example, by different cooling of one or more reaction zones and/or by intermediate cooling of the stream of material between several reaction zones, for example between 2 reaction zones. The mean temperature and the exit temperature can further be regulated by, for example, varying the temperature at which the reaction mixture enters the etherification stage and, where relevant, by recycling bleed-streams, and/or by quenching the stream of material or of bleed-streams in the etherification stage.

The etherification according to the invention can be carried out under atmospheric pressure. However, it is advantageous to work under slightly superatmospheric pressure, for example at pressures of from 1.01 to 30 bar, especially from 2 to 20 bar. Depending on the pressure and temperature, the C$_4$-hydrocarbon mixture containing isobutene may be employed for the reaction as a liquid or a gas. Preferably, a liquid C$_4$-hydrocarbon mixture containing isobutene is employed. The etherification can be carried out batchwise. In that case, the reaction time is in general from 1 minute to 5 hours. Preferably, however, the etherification is carried out continuously, in which case the ratio of the reactor volume in liters to the throughput in L/hr is in general from 0.01 to 5 hours, preferably from 0.3 to 1 hour.

For the etherification, the weight ratio of primary $C_3$- or $C_4$-alcohol to the isobutene contained in the $C_4$-hydrocarbon mixture is in general from 100:1 to 1:1, preferably from 20:1 to 1.2:1, especially from 4:1 to 1.3:1.

The reaction mixture which is obtained after the etherification and which as a rule still contains the excess primary $C_3$- or $C_4$-alcohol added for the etherification, is advantageously separated by conventional distillation without interpolating a water wash, in which case the top product obtained is a substantially isobutene-free $C_4$-hydrocarbon mixture raffinate, which in general contains not more than 5 percent by weight, preferably not more than 2.5 percent by weight, in particular not more than 1.5 percent by weight, of isobutene. In addition, the top product from the distillation in general contains at most 0.5% by weight, preferably at most 0.02% by weight, especially at most 0.005% by weight, of the primary $C_3$- or $C_4$-alcohol and, in general, at most 0.005% by weight, preferably at most 0.001% by weight, in particular at most 0.0005% by weight, of the tertiary ether.

The bottom product of the distillation of the reaction mixture obtained after the etherification is the tertiary ether, which may or may not contain excess primary $C_3$-alcohol or $C_4$-alcohol.

In the second stage of the process, the tertiary ether obtained is then decomposed into isobutene and primary $C_3$- or $C_4$-alcohol in the presence of an acid catalyst at an elevated temperature. The starting product used for the decomposition stage may be a tertiary ether which is virtually free from primary $C_3$- or $C_4$-alcohol and which is obtained, for example, by carrying out the etherification with an amount of primary $C_3$- or $C_4$-alcohol which at most corresponds to the stoichiometrically required amount of alcohol, or by removing, for example by distillation, excess primary $C_3$- or $C_4$-alcohol from the bottom product obtained after distillation of the etherification reaction mixture. Preferably, the tertiary ether obtained as the bottom product after distillative removal of the $C_4$-hydrocarbon mixture raffinate is employed for the decomposition without additionally removing any excess $C_3$- or $C_4$-alcohol. It is, however, also possible to remove only a proportion of the excess $C_3$- or $C_4$-alcohol.

To carry out the decomposition, the tertiary ether is vaporized and brought into contact with the acid catalyst in the vapor phase. Examples of suitable acid catalysts are ion exchangers in the hydrogen form, eg. sulfonated coals, zeolites, sulfonated phenol-formaldehyde resins, sulfonated resins derived from coumarone-indene condensation products and, in particular, sulfonated polystyrene resins, eg. nuclear-sulfonated cross-linked styrene-divinylbenzene copolymers.

The use of solid phosphoric acid catalysts which contain monophosphoric acid or, preferably, polyphosphoric acid on a solid carrier is also advantageous. Examples of suitable carriers for the phosphoric acid catalysts are alumina, silica, active charcoal, kieselguhr and pumice. Silica gel is the preferred carrier.

Other suitable acid catalysts are acid metal sulfates, eg. sodium bisulfate, calcium bisulfate, aluminum sulfates, nickel sulfate, copper sulfate, cobalt sulfate, cadmium sulfate and strontium sulfate. These acid metal sulfates may be used as such, but are preferably used on a carrier. Examples of suitable carriers are silica gel, active charcoal, alumina and pumice.

Furthermore, silica gel or alumina may also be used by themselves as catalysts for the decomposition.

In a further embodiment of the process according to the invention, the acid catalyst used for the decomposition is a metal phosphate, in particular a metal hydrogen phosphate. These phosphates may also contain phosphoric acid in excess over the stoichiometric composition of the acid metal phosphates, for example in an excess of up to 65%, preferably of up to 20%, especially of up to 10%. Examples of such metal phosphates which may be used are magnesium phosphates, calcium phosphates, strontium phosphates, barium phosphates, manganese phosphates, nickel phosphates, copper phosphates, cobalt phosphates, cadmium phosphates, iron (II) phosphates, chromium phosphates and, in particular, aluminum phosphates. The metal phosphate catalyst may be used as such or on a carrier. Examples of suitable carriers are alumina, silica, active charcoal and zinc oxide.

The amount of the acid catalyst is in general from about 0.01 to 1 kg, preferably from about 0.03 to 0.3 kg, per kg/h throughput of tertiary ether through the reactor. Preferably, fixed bed reactors are used for the decomposition of the tertiary ether.

The decomposition temperature of the tertiary ether varies depending on the nature of the acid catalyst and on the contact time, but is in general from 50° to 350° C., preferably from 80° to 300° C., especially from 100° to 250° C. If metal phosphates or phosphoric acid catalysts are used as the decomposition catalysts, the temperatures used are in general from 80° to 350° C., preferably from 90° to 260° C., especially from 100° to 210° C., and it can be advantageous if the exit temperature of the reaction mixture from the decomposition stage does not exceed 260° C. and preferably does not exceed 210° C.

Advantageously, the exit temperature of the reaction mixture from the decomposition stage of the tertiary ether is maintained above the mean temperature in the decomposition stage. In general, the temperature at which the reaction mixture leaves the decomposition stage is from 3° to 30° C., preferably from 5° to 20° C., especially from 7° to 15° C., above the mean temperature in the decomposition stage. The latter is advantageously determined by appropriate use of equation (1) or (2) given above. The mean temperature in the decomposition stage, and the exit temperature from the latter, can be adjusted by, for example, supplying different amounts of heat at the various points of the decomposition stage.

The contact time of the vaporized tertiary ether is advantageously from 0.1 to 20 seconds, preferably from 1 to 10 seconds.

The tertiary ether can be decomposed under atmospheric pressure. However, it is also possible to work under superatmospheric pressure, for example at pressures of up to 30 bar, preferably up to 20 bar, especially from 1 to 10 bar. Equally, however, the decomposition can also be carried out under reduced pressure.

The decomposition is in general carried out continuously. The isobutene is isolated, advantageously by distillation, from the reaction mixture obtained on decomposition, which contains isobutene and primary $C_3$- or $C_4$-alcohol as the products. In general, the isobutene is taken off as the top product of the distillation, without interpolating a water wash, and contains at most 500 ppm by weight, preferably at most 100 ppm by weight, of primary $C_3$- or $C_4$-alcohol. Advantageously, the isobutene has a purity of at least 99.3% by weight, preferably at least 99.5% by weight, but purities of more than 99.8% by weight can also be achieved without special effort. The product which remains and which essentially contains the primary $C_3$- and $C_4$-alcohol, is advantageously recycled to the etherification stage.

If a continuous process is used, and the primary $C_3$- or $C_4$-alcohol obtained after decomposing the tertiary ether, and then working up the reaction mixture, is recycled to the etherification zone, it can be advantageous, in the novel process, if using isobutanol as the $C_4$-alcohol, to take off an isobutanol bleed stream from the main isobutanol stream, in order to remove impurities which may have accumulated. Advantageously, the bleed stream is from 0.1 to 10 percent by weight, preferably from 0.5 to 5 percent by weight, of the main isobutanol stream. In an advantageous embodiment of the process, the isobutanol bleed stream is dehydrated to isobutene by conventional methods in the presence of a dehydration catalyst, as a result of which the yield of isobutene is additionally increased, in contrast to the conventional processes.

Advantageously, the dehydration is carried out in the gas phase, over a catalyst. Examples of suitable catalysts are silica gel, thorium oxide, titanium(IV) oxide and especially alumina. In general, the dehydration is carried out at from 250° to 450° C., preferably from 300° to 400° C.

The Figure diagramatically illustrates an embodiment of the process according to the invention. The isobutene-containing $C_4$-hydrocarbon mixture (fed through line 1) and the primary $C_3$- or $C_4$-alcohol (fed through line 2) are mixed and the resulting mixture is fed through line 3 to the etherification stage 4 which consists of several (for example from 3 to 5) reactors which are arranged in series and which contain the acid condensing agent, for example an ion exchanger. Advantageously, the reactors are fixed bed reactors, for example a flow tube, a loop reactor or a combination of the two types. However, other types of reactor, for example a fluidized bed reactor, stirred kettle or stirred kettle cascade, can also be used. The reaction temperatures in the reactors which are arranged in series are set so that the first reactor, to which the mixture of starting materials is initially fed, is at the highest reaction temperature, whilst the subsequent reactors are each set to a low temperature than the immediately preceding reactor. Accordingly, the last of the reactors in the series is at the lowest reaction temperature, and after completion of the reaction the mixture is taken from this reactor through line 5 and fed to a first distillation column 6. At the top of the distillation column, substantially isobutene-free $C_4$-hydrocarbon mixture (raffinate) is taken off through line 7. The tertiary ether which is obtained as the bottom product of the distillation column 6 and which may still contain excess primary $C_3$- or $C_4$-alcohol, is next fed to the vaporizer 9 through line 8, and after vaporization is introduced, through line 10, into the decomposition stage 11, which contains the acid catalyst. In general, fixed bed reactors are used for the decomposition stage 11. However, other types of reactors, eg. fluidized bed reactors, may also be used. The mixture of isobutene and primary $C_3$- or $C_4$-alcohol which is taken off the decomposition stage 11 is fed through line 12 into the distillation column 13, where very pure isobutene is obtained as the top product and is taken off through line 14. The primary $C_3$- or $C_4$-alcohol which is obtained as the bottom product is recycled to the etherification reactor 4 via lines 15 and 2, with or without supplementary addition of primary $C_3$- or $C_4$-alcohol through line 16. Advantageously, a small bleed stream, containing primary $C_3$- or $C_4$-alcohol, is taken off through line 17 in order to remove impurities which may have formed, such as diisobutyl ether, diisobutene or triisobutene. If isobutanol is used as the $C_3$- or $C_4$-alcohol, this bleed stream may be fed to a dehydration reactor, in which isobutene is additionally obtained.

Using the process according to the invention, very pure isobutene is obtained, which is in particular suitable for the preparation of high molecular weight isobutene polymers.

The Examples which follow illustrate the invention.

EXAMPLE

The etherification was carried out using a $C_4$-hydrocarbon mixture, which represents the residue (raffinate I) of a $C_4$-fraction—obtained from an ethylene plant—from which the butadiene has been extracted. After the butadiene extraction, the $C_4$-hydrocarbon mixture had the following composition:

| | |
|---|---|
| Isobutane | 1.9% by volume |
| n-Butane | 8.1% by volume |
| Isobutene | 46.0% by volume |
| But-1-ene | 26.7% by volume |
| trans-But-2-ene | 10.1% by volume |
| cis-But-2-ene | 7.0% by volume |
| Buta-1,3-diene | 0.2% by volume |

A mixture of 2,000 g per hour of this $C_4$-hydrocarbon mixture and 2,150 g per hour of technical-grade isobutanol was fed into the etherification stage, which consisted of three tubular reactors connected in series and filled with a sulfonated styrene-divinylbenzene copolymer resin in the hydrogen form (Lewatit SPC 118), the first reactor being kept thermostatically at a temperature $T_1 = 80°$ C., the second reactor at $T_2 = 60°$ C. and the third reactor at $T_3 = 40°$ C.

The ratio of the volumes V of the reactors was $V_1:V_2:V_3 = 1:1.4:4$, and the residence time, based on the total empty reactor volume, was 320 s. The mean temperature in the etherification stage was 50.6° C. The reaction mixture obtained was fed to a distillation column, and at the top of the column a stream of unconverted hydrocarbons (raffinate II), containing isobutane, n-butane, but-1-ene, trans-but-2-ene, cis-but-2-ene and buta-1,3-diene, was taken off. Raffinate II contained less than 2% by weight of isobutene. It was virtually free from isobutanol and could therefore be used directly, without additional purification operations, for example without interpolation of a water wash, as the starting material for further reactions. The bottom product of the distillation column was isobutyl tert.-butyl ether, which additionally contained excess isobutanol.

COMPARATIVE EXAMPLE

The etherification was carried out as described in Example 1, but the three reactors were all kept at the same temperature of 50.6° C., which corresponded to the mean temperature in Example 1. The raffinate II obtained at the top of the distillation column contained 3.0% by weight of isobutene. On thermostatically keeping the three reactors at $T_1=40°$ C., $T_2=60°$ C. and $T_3=80°$ C., the raffinate II obtained even contained more then 3.4% by weight of isobutene.

The bottom product which was obtained from the distillation in Example 1 and which contained isobutyl ter.-butyl ether and the excess isobutanol was vaporized and passed into a heated tubular reactor in which the ether was decomposed. The reactor was filled with a catalyst which had been prepared by absorbing phosphoric acid on silica gel and then heating. The exit temperature of the reaction product from the decomposition stage was 190° C. The mean temperature in the decomposition stage was 180° C. The reaction product was fed into a distillation column at the top of which isobutene was obtained, whilst at the bottom isobutanol was obtained and was recycled to the etherification stage. The yield of isobutene, which was obtained in a very pure form, was 97.6%, based on the isobutene contained in the $C_4$-hydrocarbon mixture employed in Example 1.

If the mean temperature maintained in the decomposition stage was higher than the exit temperature of the reaction mixture from the said stage, an isobutene product of lower purity and/or an isobutanol bottom product, of the distillation column, having a higher content of isobutyl tert.-butyl ether was obtained.

We claim:

1. A process for isolating isobutene from $C_4$-hydrocarbon mixtures containing isobutene which comprises
    (a) reacting the mixture with a primary $C_3$- or $C_4$-alcohol in the presence of an acid condensing agent, to form the tertiary ether,
    (b) taking the reaction mixture off at the exit of the etherification stage at a temperature from 3° to 30° C. lower than the mean temperature in the etherification stage,
    (c) separating off the unconverted hydrocarbons, and
    (d) composing the tertiary ether in the presence of an acid catalyst.

2. The process of claim 1, wherein the reaction mixture leaves at the exit of the etherification stage at a reaction temperature which is from 5° to 20° C. lower than the mean temperature in the etherification stage.

3. The process of claim 1, wherein the temperature at which the reaction mixture exits from the stage in which the tertiary ether formed is decomposed is higher than the mean temperature in the decomposition stage.

4. The process of claim 1 or 2, wherein from 2 to 10 fixed bed reactors are used for the etherification stage.

5. The process of claim 1, wherein an ion exchanger in its hydrogen form is used as the acid condensing agent for the etherification stage.

6. The process of claim 1, wherein from 2 to 6 reaction zones are arranged in series in the etherification stage.

7. The process of claim 1 or 2 or 4 or 5 or 6, wherein the conversion of the isobutene, contained in the $C_4$-hydrocarbon mixture, to the $C_3$- or $C_4$-alkyl tert.-butyl ether in the etherification reaction is not less than 90%.

8. The process of claim 4, wherein the reaction mixture exits from the etherification stage at a reaction temperature which is from 7° to 15° C. lower than the mean temperature in the etherification stage.

9. The process of claim 5, wherein from 2 to 6 fixed bed reaction zones are arranged in series.

10. The process of claim 9, wherein the primary $C_3$- or $C_4$-alcohol and the $C_4$-hydrocarbon mixture are first fed to the etherification stage, the reaction mixture obtained from the latter is then distilled, without interpolation of a water wash, in a first distillation zone, whereby a substantially isobutene-free top product containing the unconverted hydrocarbons is obtained while the tertiary ether formed, which may or may not contain excess primary $C_3$- or $C_4$-alcohol, is taken off as the bottom product, the latter is then fed to the decomposition stage, in which the tertiary ether is decomposed at an elevated temperature into isobutene and primary $C_3$- or $C_4$-alcohol, the mixture of isobutene and primary $C_3$- or $C_4$-alcohol is fed to a second distillation zone, where, without interpolation of a water wash, isobutene containing at most 500 ppm by weight of primary $C_3$- or $C_4$-alcohol is obtained as a top product, while primary $C_3$- or $C_4$-alcohol is taken off as the bottom product, and the latter is recycled to the etherification stage.

* * * * *